(12) United States Patent
Wang et al.

(10) Patent No.: US 8,503,751 B2
(45) Date of Patent: Aug. 6, 2013

(54) METHOD AND APPARATUS FOR IMPLEMENTING FAT-WATER SEPARATION IN A MAGNETIC RESONANCE SYSTEM

(75) Inventors: Zhen Kui Wang, Shenzhen (CN); Dong Mei Wu, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 627 days.

(21) Appl. No.: 12/729,552

(22) Filed: Mar. 23, 2010

(65) Prior Publication Data

US 2010/0239149 A1 Sep. 23, 2010

(30) Foreign Application Priority Data

Mar. 23, 2009 (CN) .......................... 2009 1 0119608

(51) Int. Cl.
*G06K 9/34* (2006.01)
(52) U.S. Cl.
USPC ........................................ 382/131; 382/128
(58) Field of Classification Search
USPC ............ 324/307, 309; 382/131, 128; 600/409
See application file for complete search history.

(56) References Cited

U.S. PATENT DOCUMENTS

| | | | | |
|---|---|---|---|---|
| 4,870,361 A * | 9/1989 | In Den Kleef et al. | ....... | 324/309 |
| 5,594,336 A * | 1/1997 | Gullapalli et al. | ............ | 324/309 |
| 5,856,744 A * | 1/1999 | Block et al. | ................... | 324/309 |
| 5,909,119 A * | 6/1999 | Zhang et al. | .................. | 324/309 |
| 6,263,228 B1 * | 7/2001 | Zhang et al. | .................. | 600/409 |
| 6,583,623 B1 * | 6/2003 | Kwok et al. | ................... | 324/307 |
| 6,603,990 B2 * | 8/2003 | Zhang et al. | .................. | 600/410 |
| 6,856,134 B1 * | 2/2005 | Reeder et al. | ................. | 324/309 |
| 7,141,972 B2 * | 11/2006 | Avram et al. | ................. | 324/307 |
| 7,148,685 B2 * | 12/2006 | Block et al. | ................... | 324/307 |
| 7,298,144 B2 * | 11/2007 | Reeder et al. | ................. | 324/307 |
| 7,863,895 B2 * | 1/2011 | Ma | ............................... | 324/309 |
| 2010/0272337 A1 * | 10/2010 | Shirai et al. | ................... | 382/131 |

* cited by examiner

*Primary Examiner* — Gerald J. O'Connor
*Assistant Examiner* — Teresa Woods
(74) *Attorney, Agent, or Firm* — Schiff Hardin LLP

(57) ABSTRACT

In a magnetic resonance (MR) method and apparatus for implementing fat-water separation, MR data acquired representing one in-phase image and two out-of-phase images, phase differences between the two out-of-phase images are calculated, and the phases caused by the inhomogeneity of a magnetic field in the two out-of-phase images are calculated by using the phase differences; correcting linear phase differences in the in-phase image caused by eddy currents, by using the two corrected out-of-phase images. Calculations are then made on the basis of the three corrected images to obtain water and fat images. This method and apparatus effectively eliminate the adverse effects caused by the eddy currents in the currently available implementing process of the three points Dixon method.

7 Claims, 3 Drawing Sheets

METHOD AND APPARATUS FOR IMPLEMENTING FAT-WATER SEPARATION IN A MAGNETIC RESONANCE SYSTEM

BACKGROUND OF THE INVENTION

1. Field of the Invention

The present invention relates to magnetic resonance (MR) technology and, particularly to a method and an apparatus for implementing fat-water separation in an MR system.

2. Description of the Prior Art

The Dixon method has been used widely for a long time to separate MR signals respectively originating from fat and water, due to its relatively good fat-water separation function.

The three-point Dixon method is an improvement to the basic Dixon method, and in this method, the normally adopted mode of collecting the echo signals is out-of-phase—in-phase—out-of-phase, so as to acquire two out-of-phase images and one in-phase image, and phase differences caused by the inhomogeneity of a magnetic field are calculated on the basis of the two out-of-phase images, to implement the phase correction of in the two out-of-phase images, and finally they are combined with the in-phase image to produce the water and fat images.

In the three-point Dixon method, the time interval between two echo signals is very small, for example, for a 1.5 T MR system, the time interval between two echo signals is only 2.38 ms, and this puts a very high requirement to the gradient performance of the MR system. Normally, the bipolar gradient can substantially meet the requirement. As shown in FIGS. 1 and 2, FIGS. 1 and 2 are a water image and a fat image respectively which are produced by using the currently available three-point Dixon method to carry out the water-fat separation.

SUMMARY OF THE INVENTION

An object of the present invention is to provide an method for implementing fat-water separation, which can effectively remove the adverse effects caused by the eddy currents.

Another object of the present invention is to provide an apparatus for implementing fat-water separation, which can effectively remove the adverse effects caused by the eddy currents.

The above objects are achieved in accordance with the invention by a method for implementing fat-water separation, including acquiring data representing one in-phase image and two out-of-phase images of a subject, calculating phase differences between the two out-of-phase images, and correcting the phases caused by the inhomogeneity in a magnetic field in the two out-of-phase images by using the phase differences, correcting linear phase differences caused by eddy currents in the in-phase image by using the two corrected out-of-phase images, and making calculations based on the three corrected images to obtain the water and fat images.

Preferably, the step of acquiring one in-phase image and two out-of-phase images proceeds by acquiring one out-of-phase image, one in-phase image and the other out-of-phase image in succession by using a bipolar gradient mode in the direction of collecting the echo signals.

Preferably, the step of calculating the phase differences of the two out-of-phase images and correcting the phases caused by the inhomogeneity of the magnetic field in the two out-of-phase images by using the phase differences proceeds by calculating a product of S1* and S3 to obtain a phase ϕ31 corresponding to the product, wherein * represents a conjugate operation; said S1 and S3 represent the two out-of-phase images acquired, and multiplying $$e^{i\frac{\varphi 31}{2}}$$

with said S1, and multiplying $$e^{i\frac{\varphi 31}{2}}$$

with said S3, to obtain the two corrected out-of-phase images S1' and S3'.

Preferably, the step of correcting the linear phase differences caused by the eddy currents in the in-phase image by using the two corrected out-of-phase images proceeds by calculating a result S32 of (S3'×S2*)×(S2×S1'*)* to obtain a phase $\phi_{ecc}$ corresponding to S32; wherein S2 represents the acquired in-phase image, S1' and S3' represent the two corrected out-of-phase images, and * represents a conjugate operation, and multiplying S2 by $\phi_{ecc}$ to obtain the corrected in-phase image S2'.

Preferably, the step of making calculations based on the three corrected images to obtain the fat and water images proceeds by calculating the quotient A of the sum of S1' and S3' divided by 2; dividing the sum of S2' and A by 2 and taking the absolute value thereof, so as to obtain the water image, and dividing the difference between the S2' and A by 2 and taking the absolute value thereof, so as to obtain the fat image, wherein, S1' and S3' represent the two corrected out-of-phase images, and S2' represents the corrected in-phase image.

An apparatus for implementing fat-water separation has a magnetic resonance data acquisition unit for acquiring MR data representing one in-phase image and two out-of-phase images of a subject, a first correcting unit for calculating phase differences of said two out-of-phase images, and correcting the phases caused by the inhomogeneity of a magnetic field in the two out-of-phase images by using the phase differences, a second correcting unit for correcting linear phase differences caused by eddy currents in the in-phase image by using the two corrected out-of-phase images, and a calculating unit for making calculations based on the three corrected images to obtain the water and fat images.

Preferably, the first correcting unit includes a first calculating subunit for calculating a product of S1* and S3 to obtain a phase ϕ31 corresponding to the product; wherein * represents a conjugate operation, and S1 and S3 represent the two acquired out-of-phase images, and a second calculating subunit for multiplying $$e^{i\frac{\varphi 31}{2}}$$

by S1, and multiplying $$e^{i\frac{\varphi 31}{2}}$$

by S3, to obtain the two corrected out-of-phase images S1' and S3'.

Preferably, the second correcting unit includes a third calculating subunit for calculating a result S32 of (S3'×S2*)×(S2×S1'*)* to obtain a phase $\phi_{ecc}$ corresponding to S32;

wherein S2 represents the acquired in-phase image, said S1' and S3' represent the two corrected out-of-phase images, and * represents a conjugate operation, and a fourth calculating subunit for multiplying S2 by $\phi_{ecc}$ to obtain a corrected in-phase image S2'.

Preferably, the calculating unit includes a fifth calculating subunit for calculating the quotient A of the sum of S1' and S3' divided by 2, and then dividing the sum of S2' and A by 2 and taking the absolute value thereof, so as to obtain the water image, and a sixth calculating subunit for calculating the quotient A of the sum of S1' and S3' divided by 2, and dividing the difference between S2' and A by 2 and taking the absolute value thereof, so as to obtain the fat image, wherein S1' and S3' represent the two corrected out-of-phase images, and S2' represents the corrected in-phase image.

By using the solution of the present invention, a series of arithmetic operations, firstly corrects the phases caused by the inhomogeneity of the magnetic field in the two out-of-phase images, and then corrects the linear phase differences caused by the eddy currents in the in-phase image by using the two corrected out-of-phase images, so as to make the three images in phase with each other, thereby eliminating the adverse effects caused by the eddy currents, and thereby improving the image quality significantly.

DESCRIPTION OF THE PREFERRED EMBODIMENTS

Targeting the problems in the prior art, the present invention concerns a new method for implementing fat-water separation, namely an improved three-point Dixon method, so as to eliminate the adverse effects caused by eddy currents in the currently available three-point Dixon methods.

In order to achieve the objects, technical solutions and advantages of the present invention more apparent, the present invention will be further described in detail below in conjunction with accompanying drawings and embodiments. It should be understood that the embodiments described herein are merely to explain the present invention, and they are not to limit the present invention.

Figure 3:
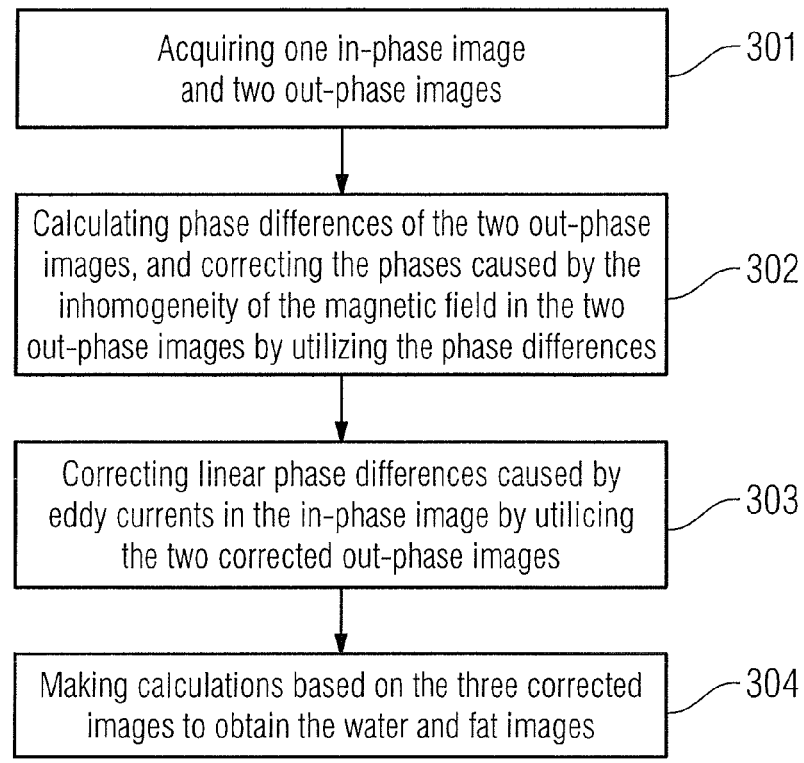
FIG. 3 is a flowchart of an embodiment of the method of the present invention.

FIG. 3 is a flowchart of an embodiment of the method of the present invention. As shown in FIG. 3, it comprises the following steps:

Step 301: acquiring one in-phase image and two out-of-phase images.

In this step, one out-of-phase image S1, one in-phase image S2 and another out-of-phase image S1 are acquired in succession using a bipolar gradient mode in the direction of collecting the echo signals. The particular process of how to acquire them is known in the art, and will not be described here redundantly.

Considering that in practical applications, the above three images will be affected by both the eddy currents and the inhomogeneity of a magnetic field, namely being affected by both linear phase differences caused by the eddy currents and the phases caused by the inhomogeneity of the magnetic field, the acquired three images can therefore be expressed respectively in an image space as follows (the effects of T2* are ignored):

$$S1=(W-F)e^{i(\phi_0-\Delta\phi+\phi_1)} \quad (1)$$

$$S2=(W+F)e^{i(\phi_0+\phi_2)} \quad (2)$$

$$S3=(W-F)e^{i(\phi_0+\Delta\phi+\phi_3)} \quad (3)$$

wherein W and F represent the water image and fat image respectively; $\Delta\phi$ represents a phase caused by the inhomogeneity of the magnetic field, and this parameter varies with time; $\phi 1, \phi 2, \phi 3$ represent the linear phase differences caused by the eddy currents respectively; $\phi_0$ represents an inherent phase; S1 and S3 represent two out-of-phase images, and S2 represents the in-phase image.

The mode of expression of the above three images is known in the art, and will not be described here redundantly.

Step 302: calculate the phase differences of the two out-of-phase images, and correct the phases caused by the inhomogeneity of the magnetic field in two out-of-phase images using the phase differences.

In this step, aiming at the two out-of-phase images S1 and S3 acquired in Step 301, the following operations are executed respectively:

firstly, calculating a product of S1* and S3, to obtain a phase $\phi 31=2\Delta\phi+\phi 3-\phi 1$ corresponding to the product; wherein * represents the conjugate operation;

then, multiplying $$e^{i\frac{\varphi 31}{2}}$$

with S1, and multiplying $$e^{-i\frac{\varphi 31}{2}}$$

with S2, to obtain two corrected out-of-phase images S1' and S3', that is to say:

$$S1' = (W - F)e^{i(\phi_0+\frac{\varphi_1+\varphi_3}{2})}; \quad (4)$$

$$S3' = (W - F)e^{i(\phi_0+\frac{\varphi_1+\varphi_3}{2})}; \quad (5)$$

It can be seen that, after the above processing, the phase caused by the inhomogeneity of the magnetic field, namely $\Delta\phi$, has been eliminated, but the linear phase differences caused by the eddy currents are still present, and therefore it is necessary to perform a further processing.

Step 303: correcting the linear phase differences caused by the eddy currents in the in-phase image by using the two corrected out-of-phase images.

Firstly, calculating the product S32:

$$S32=(S3'\times S2^*)\times(S2\times S1'^*) \quad (6)$$

thus getting the phase $\phi_{ecc}$ corresponding to S32;

$$\phi_{ecc} = \frac{\varphi 1 + \varphi 3}{2} - \varphi 2 - \left(\varphi 2 - \frac{\varphi 1 + \varphi 3}{2}\right); \quad (7)$$

then, multiplying S2 with $\phi_{ecc}$, to obtain the corrected in-phase image S2', that is:

$$S2' = (W+F)e^{i(\phi_0 + \frac{\varphi_1 + \varphi_3}{2})}. \quad (8)$$

By then, the phases of S1', S2' and S3' are the same, and the effects of the eddy currents have been eliminated.

Step 304: making calculations based on the three corrected images to obtain the water and fat images.

After the processing in Steps 302 and 303, both the phases caused by the inhomogeneity of the magnetic field and the linear phase differences caused by the eddy currents are corrected, and therefore in this step, the final water and fat images required can be calculated on the basis of the three corrected images, so as to implement the fat-water separation. The detailed calculating can be as follows:

$$|W| = \left|\left(\frac{S1' + S3'}{2} + S2'\right)/2\right|; \quad (9)$$

$$|F| = \left|\left(S2' - \frac{S1' + S3'}{2}\right)/2\right|; \quad (10)$$

|W| and |F| represent respectively the water image and the fat image after implementing the fat-water separation.

The subsequent operations of how to perform the processing on the acquired water and fat images are not relevant to the present invention, and will not be introduced.

Figure 1:
FIG. 1 is a water image acquired by using a currently available three-point Dixon method to perform the fat-water separation.
Figure 2:
FIG. 2 is a fat image acquired by using the currently available three-point Dixon method to perform the fat-water separation.
Figure 4:
FIG. 4 is a water image acquired by using a three-point Dixon method of the present invention to perform the fat-water separation.
Figure 5:
FIG. 5 is a fat image acquired by using a three-point Dixon method of the present invention to perform the fat-water separation.

FIGS. 4 and 5 are respectively water and fat images obtained by using the three-point Dixon method of the present invention to perform the fat-water separation (FIG. 4 is the water image, and FIG. 5 the fat image); it can be seen that, compared with the water and fat images produced by using an currently available three-point Dixon method to perform the fat-water separation as shown in FIGS. 1 and 2, said method of the present invention can better suppress the fat signals, thus improving the image quality.

Figure 6:
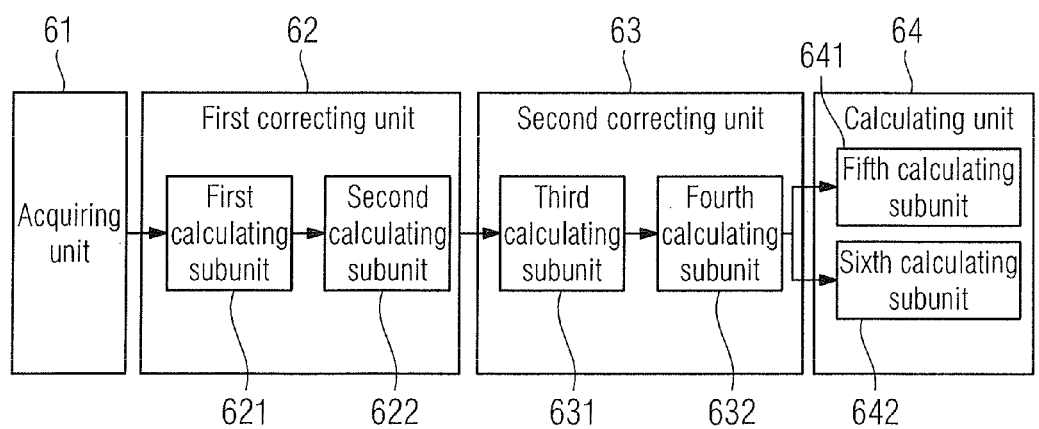
FIG. 6 is a schematic structural diagram of an embodiment of the apparatus of the present invention.

Based on the above method, FIG. 6 is a schematic structural diagram of an embodiment of the apparatus of the present invention. As shown in FIG. 6, the apparatus comprises:

a data acquisition unit 61 for acquiring MR data representing one in-phase image and two out-of-phase images;

a first correcting unit 62 for calculating the phase differences of the two out-of-phase images, and correcting the phases caused by the inhomogeneity of a magnetic field in the two out-of-phase images by using the phase differences;

a second correcting unit 63 for correcting linear phase differences caused by eddy currents in the in-phase image by using the two corrected out-of-phase images; and a calculating unit 64 for making calculations based on the three corrected images to obtain the water and fat images.

In this case, the first correcting unit 62 can particularly include:

a first calculating subunit 621 for calculating a product of S1* and S3 to obtain a phase $\phi 31$ corresponding to the product; wherein represents a conjugate operation, and S1 and S3 represent the two acquired out-of-phase images; and a second calculating subunit 622 for multiplying $$e^{i\frac{\varphi 31}{2}}$$

with S1, and multiplying $$e^{-i\frac{\varphi 31}{2}}$$

with S3, to obtain the two corrected out-of-phase images S1' and S3'.

The second correcting unit 63 can particularly include:

a third calculating subunit 631 for calculating a result S32 of (S3'×S2*)×(S2×S1'*)* to obtain a phase $\phi_{ecc}$ corresponding to S32; wherein said S2 represents the acquired in-phase image; and a fourth calculating subunit 632 for multiplying S2 with $\phi_{ecc}$ to obtain a corrected in-phase image S2'.

The calculating unit 64 can particularly include:

a fifth calculating subunit 641 for calculating the quotient A of the sum of S1' and S3' divided by 2, and then dividing the sum of S2' and said A by 2 and taking the absolute value thereof, so as to obtain the water image; and a sixth calculating subunit 642 for calculating the quotient A of the sum of S1' and S3' divided by 2, and dividing the difference between S2' and said A by 2 and taking the absolute value thereof, so as to obtain the fat image.

For a particular workflow of the embodiment of the apparatus shown in FIG. 6, reference can be made to the corresponding description of the embodiment of the method shown in FIG. 3, and it need not be described here redundantly.

In summary, by using the technical solutions of the present invention, the adverse effects caused by the inhomogeneity of the magnetic field and the eddy currents are eliminated quite well, thus significantly improving the quality of the images after the fat-water separation; and furthermore, the present invention also has the advantage of being easy to implement.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for implementing fat-water separation, comprising the steps of:
   acquiring an in-phase image and two out-of-phase images of a subject;
   in a processor, automatically calculating phase differences between the two out-of-phase images, and correcting the phases caused by the inhomogeneity of a magnetic field in the two out-of-phase images by using the phase differences;
   in a processor, automatically correcting linear phase differences caused by eddy currents in the in-phase image by using the two corrected out-of-phase images by calculating a result S32 of (S3'×S2*)×(S2×S1'*)* to obtain a phase $\phi_{ecc}$ corresponding to S32; wherein S2 represents the acquired in-phase image, S1' and S3' represent the two corrected out-of-phase images, and * represents the conjugate operation, and multiplying S2 by $\phi_{ecc}$ to obtain an in-phase image S2' after correction; and in a processor, making calculations based on the three corrected images to obtain water and fat images.

2. The method as claimed in claim 1, wherein the step of acquiring the images comprises:

acquiring in succession one out-of-phase image, one in-phase image and another out-of-phase image by using a bipolar gradient mode to read out echo signals.

3. The method as claimed in claim 1, wherein the step of calculating the phase differences of said two out-of-phase images and correcting them by using the phase differences comprises:

calculating a product of S1* and S3 to obtain a phase φ31 corresponding to the product, wherein * represents a conjugate operation, S1 and S3 represent the acquired two out-of-phase images; and
multiplying $$e^{i\frac{\varphi 31}{2}}$$

by S1, and multiplying $$e^{-i\frac{\varphi 31}{2}}$$

by S3, to obtain the two corrected out-of-phase images S1' and S3'.

4. The method as claimed in claim 1, wherein the step of calculating to obtain the fat and water images comprises:

calculating the quotient A of the sum of S1' and S3' divided by 2; dividing the sum of S2' and A by 2 and taking the absolute value thereof, to obtain the water image; and dividing the difference between S2' and A by 2 and taking the absolute value thereof, to obtain the fat image; wherein S1' and S3' represent the two corrected out-of-phase images, and S2' represents the corrected in-phase image.

5. A magnetic resonance apparatus for implementing fat-water separation, comprising:

a magnetic resonance data acquisition unit having a basic field magnet that generates a magnetic field exhibiting an inhomogeneity, said magnetic resonance data acquisition unit being configured to interact with a subject therein, using said magnetic field, to acquire one in-phase image and two out-of-phase images of the subject;

a processor configured to calculate phase differences between said two out-of-phase images, and to correct the phases caused by said inhomogeneity of the magnetic field in said two out-of-phase images by using the phase differences;

said processor being configured to correct linear phase differences caused by eddy currents in said in-phase image by using the two corrected out-of-phase images by calculating a result S32 of (S3'×S2*)×(S2×S1'*)* to obtain a phase $\phi_{ecc}$ corresponding to S32; wherein S2 represents the acquired in-phase image, S1' and S3' represent the two corrected out-of-phase images, and * represents the conjugate operation, and multiplying S2 by $\phi_{ecc}$ to obtain an in-phase image S2' after correction; and said processor being configured to make calculations based on the three corrected images to obtain data representing water and fat images at an output of said processor.

6. The apparatus as claimed in claim 5, wherein said processor being configured to:

calculate a product of S1* and S3 to obtain a phase φ31 corresponding to the product; wherein * represents a conjugate operation, and S1 and S3 represent the two acquired out-of-phase images; and
multiply $$e^{i\frac{\varphi 31}{2}}$$

with S1, and multiply $$e^{-i\frac{\varphi 31}{2}}$$

with S3, to obtain the two corrected out-of-phase images S1' and S3'.

7. The apparatus as claimed in claim 5 wherein said processor is configured to:

calculate the quotient A of the sum of S1' and S3' divided by 2, and then divide the sum of S2' and A by 2 and taking the absolute value thereof, to obtain the water image; and calculate the quotient A of the sum of S1' and S3' divided by 2, and divide the difference between S2' and A by 2 and take the absolute value thereof, to obtain the fat image; said S1' and S3' represent the two corrected out-of-phase images, and S2' represents the corrected in-phase image.

* * * * *